(12) United States Patent
Chardon et al.

(10) Patent No.: US 10,751,469 B2
(45) Date of Patent: Aug. 25, 2020

(54) COMPUTER CONTROLLED PEDIATRIC REGIONAL ANESTHESIA

(71) Applicant: Northwestern University, Evanston, IL (US)

(72) Inventors: Matthieu Kevin Chardon, Chicago, IL (US); Michael David Johnson, Evanston, IL (US); Charles Heckman, II, Evanston, IL (US); Santhanam Suresh, Evanston, IL (US)

(73) Assignee: Northwesten University, Evanston, IL (US)

( * ) Notice: Subject to any disclaimer, the term of this patent is extended or adjusted under 35 U.S.C. 154(b) by 37 days.

(21) Appl. No.: 15/947,390

(22) Filed: Apr. 6, 2018

(65) Prior Publication Data

US 2018/0326148 A1   Nov. 15, 2018

Related U.S. Application Data

(60) Provisional application No. 62/482,852, filed on Apr. 7, 2017.

(51) Int. Cl.
| | |
|---|---|
| *A61M 5/172* | (2006.01) |
| *A61M 5/14* | (2006.01) |
| *A61M 19/00* | (2006.01) |
| *A61B 5/00* | (2006.01) |
| *A61B 5/04* | (2006.01) |

(52) U.S. Cl.
CPC ............ *A61M 5/1723* (2013.01); *A61M 5/14* (2013.01); *A61B 5/04001* (2013.01); *A61B 5/4824* (2013.01); *A61B 5/4848* (2013.01); *A61B 5/6831* (2013.01); *A61B 5/6837* (2013.01); *A61M 19/00* (2013.01); *A61M 2005/1405* (2013.01); *A61M 2005/1726* (2013.01); *A61M 2202/048* (2013.01); *A61M 2230/08* (2013.01)

(58) Field of Classification Search
CPC .................. A61M 5/1723; A61M 5/14; A61M 2005/1405; A61M 2005/1726; A61M 2202/048; A61M 2230/08; A61M 19/00; A61M 31/002; A61B 5/4824; A61B 5/4848; A61B 5/04001; A61B 5/6837; A61B 5/6831; A61F 2250/0067; A61N 1/0551
See application file for complete search history.

(56) References Cited

U.S. PATENT DOCUMENTS

| 4,544,371 A | 10/1985 | Dormandy, Jr. et al. |
| 5,458,631 A | 10/1995 | Xavier |

(Continued)

OTHER PUBLICATIONS

Catterall et al., Goodman & Gilman's The Pharmacological Basis of Therapeutics, 12e (eds. Brunton, L. L., Chabner, B. A. & Knollmann, B. C.) (The McGraw-Hill Companies, 2011), TOC Only.

(Continued)

*Primary Examiner* — Bhisma Mehta
*Assistant Examiner* — Rachel T. Smith
(74) *Attorney, Agent, or Firm* — Casimir Jones SC; David W. Staple

(57) ABSTRACT

A drug delivery and monitoring device comprising a nerve stimulating element configured to deliver an electric stimulus, a recording element configured to detect a compound action potential, and a drug-delivery element.

14 Claims, 11 Drawing Sheets

(56) References Cited

U.S. PATENT DOCUMENTS

| | | | |
|---|---|---|---|
| 5,487,756 A * | 1/1996 | Kallesoe | A61N 1/0556 |
| | | | 600/381 |
| 5,830,151 A | 11/1998 | Hadzic et al. | |
| 6,178,349 B1 | 1/2001 | Kieval | |
| 6,571,125 B2 | 5/2003 | Thompson | |
| 7,010,352 B2 | 3/2006 | Hogan | |
| 7,917,208 B2 * | 3/2011 | Yomtov | A61M 5/14276 |
| | | | 607/120 |
| 8,092,426 B2 | 1/2012 | Molnar | |
| 2007/0179508 A1 * | 8/2007 | Arndt | A61B 8/0833 |
| | | | 606/116 |
| 2017/0197076 A1 * | 7/2017 | Faltys | A61B 5/4839 |
| 2019/0366079 A1 * | 12/2019 | Ashe | A61N 1/0558 |

OTHER PUBLICATIONS

Chardon et al., Towards a real time pediatric regional anesthesia titration device. Abstract. American Society of Regional Anesthesia and Pain Medicine Annual Regional Anesthesiology & Acute Pain Medicine Meeting, Apr. 6-8, 2017, San Francisco, CA, 2 pages.

Chardon et al., Towards a real time pediatric regional anesthesia titration device. Poster presented at the American Society of Regional Anesthesia and Pain Medicine Annual Regional Anesthesiology & Acute Pain Medicine Meeting, Apr. 6-8, 2017, San Francisco, CA, 1 page.

Feldman et al., Comparative motor-blocking effects of bupivacaine and ropivacaine, a new amino amide local anesthetic, in the rat and dog. Anesth Analg. Nov. 1988;67(11):1047-52.

Gasser et al., The role of fiber size in the establishment of a nerve block by pressure or cocaine. Am. J. Physiol. 88, 581-591 (1929).

Gissen et al., Differential sensitivities of mammalian nerve fibers to local anesthetic agents. Anesthesiology. Dec. 1980;53(6):467-74.

Jöhr et al., Regional anaesthesia in neonates, infants and children: an educational review. Eur J Anaesthesiol. May 2015;32(5):289-97.

McClure et al., Ropivacaine. Br J Anaesth. Feb. 1996;76(2):300-7.

Metso et al., Compound nerve conduction velocity—a reflection of proprioceptive afferents? Clin Neurophysiol. Jan. 2008;119(1):29-32.

Patel et al., Differential fiber-specific block of nerve conduction in mammalian peripheral nerves using kilohertz electrical stimulation. J Neurophysiol. Jun. 1, 2015;113(10):3923-9.

Suresh et al., Are caudal blocks for pain control safe in children? an analysis of 18,650 caudal blocks from the Pediatric Regional Anesthesia Network (PRAN) database. Anesth Analg. Jan. 2015;120(1):151-6.

Suresh et al., Regional anaesthesia to improve pain outcomes in paediatric surgical patients: a qualitative systematic review of randomized controlled trials. Br J Anaesth. Sep. 2014;113(3):375-90.

Tsui et al., Pediatric Atlas of Ultrasound- and Nerve Stimulation-Guided Regional Anesthesia, 9-18. (Springer, 2015).

Walker et al., Peripheral nerve catheters in children: an analysis of safety and practice patterns from the pediatric regional anesthesia network (PRAN). Br J Anaesth. Sep. 2015;115(3):457-62.

Wildsmith et al., Structure-activity relationships in differential nerve block at high and low frequency stimulation. Br J Anaesth. Oct. 1989;63(4):444-52.

* cited by examiner

COMPUTER CONTROLLED PEDIATRIC REGIONAL ANESTHESIA

CROSS-REFERENCE TO RELATED APPLICATIONS

The present invention claims priority to U.S. Provisional Patent Application 62/482,852, filed Apr. 7, 2017, which is incorporated by reference in its entirety.

FIELD

Provided herein are devices, systems, and methods for delivery of regional anesthesia. In particular, provided herein are devices designed for computer-controlled delivery and dosage of anesthesic.

BACKGROUND

The use of regional anesthesia in pediatrics (pRA) has dramatically increased over the past 30 years, as it provides localized pain relief, diminishes opioid use, and facilitates earlier mobilization, enteral feeding and hospital discharge[1]. The technique is also used increasingly due to concerns about the effect of general anesthesia on brain development.

For several reasons, local anesthetic toxicity will become a major safety risk as pRA gains greater acceptance. First, dosing guidelines for children are mostly unknown and are based on expert conjecture[3-6]. Second, systemic toxic reactions present vastly differently in children than in adults, as they will not show early signs of toxicity because pRAs are mostly performed under deep sedation or general anesthesia. Finally, no tools are available to determine local anesthetic toxicity, other than observation of significant hemodynamic changes.

Improved devices and methods for delivery of pediatric anesthesia are needed.

SUMMARY

Provided herein are devices, systems, and methods for delivery of regional anesthesia. In particular, provided herein are devices designed for computer-controlled delivery and dosage of anesthesia.

For example, in some embodiments, provided herein is a drug delivery and monitoring device, comprising: at least two cuffs configured to stimulate a nerve and record a compound action potential; and a drug delivery cuff configured to deliver a drug directly to a nerve. In some embodiments, the drug delivery cuff comprises one or more of a right buckle, a left buckle, a suture guide, a drug output, a drug input, or a drug reservoir. In some embodiments, the cuffs are stimulation and recording cuffs. In some embodiments, the stimulation cuff comprises a stimulating echogenic needle configured to deliver an electrical current directly to a nerve. In some embodiments, the electrical current is between 1 and 10 amps (e.g., 1, 2, 3, 4, 5, 6, 7, 8, 9, 10, or a fraction thereof). In some embodiments, the recording cuff comprises a surface electrode.

Further embodiments provide a system, comprising: the devices described herein; and a computer system configured to calculate compound action potentials and determine a drug dose based on the compound action potentials. In some embodiments, the computer system is further configured to control the drug delivery cuff. In some embodiments, the level of anesthesia is adjusted to keep the compound action potential below a threshold level (e.g., 0.1 V or lower) (e.g., less than 0.1, 0.09, 0.08, 0.07, 0.06, 0.05, 0.04, 0.03, 0.02, 0.009, 0.005, 0.003, or lower).

Yet other embodiments provide a method of delivering a regional drug to a subject, comprising: contacting the system described herein with a nerve of a subject; and delivering the drug to the subject using the system. In some embodiments, the drug is regional anesthesia (e.g., epidural, spinal, or peripheral nerve block). In some embodiments, the patient is a pediatric patient.

In some embodiments, provided herein are drug delivery and monitoring devices, comprising: (a) a nerve stimulating element comprising a first electrode, wherein the first electrode is configured to deliver an electric stimulus; (b) a recording element comprising a second electrode, wherein the second electrode is configured to detect a compound action potential; and (c) a drug-delivery element. In some embodiments, devices further comprise a positioning element for attaching and/or securing the device to a nerve. In some embodiments, the positioning element comprises a cuff. In some embodiments, one or more of the nerve stimulating element, recording element, and drug-delivery element comprise cuffs for attachment of the device to a nerve. In some embodiments, devices comprise a drug delivery cuff. In some embodiments, the drug delivery cuff comprises one of more of a right buckle, a left buckle, a suture guide, a drug output, a drug input, and a drug reservoir. In some embodiments, devices comprise a stimulation cuff and a recording cuff. In some embodiments, the stimulation cuff comprises a stimulating echogenic needle. In some embodiments, the echogenic needle delivers an electrical current directly to a nerve. In some embodiments, the electrical current is between 1 and 10 amps. In some embodiments, the recording cuff comprises a surface electrode.

In some embodiments, provided herein are systems comprising: (a) a device described herein; and (b) a computer device (e.g., computer, tablet, CPU, phone, etc.) configured to calculate compound action potentials. In some embodiments, the computer device is further configured to determine a drug dose based on said compound action potentials. In some embodiments, computer device is further configured to control said drug delivery cuff. In some embodiments, the level of anesthesia is adjusted to keep the compound action potential below a threshold level. In some embodiments, the threshold level is 0.1 V.

In some embodiments, provided herein are methods of delivering a regional drug to a subject, comprising: (a) contacting a nerve of the subject with the system described herein; (b) delivering the drug to the subject using said system; and (c) monitoring compound action potentials. In some embodiments, methods further comprise adjusting the level of drug delivered to the nerve based on said compound action potentials. In some embodiments, the drug is regional anesthesia. In some embodiments, the regional anesthesia is epidural, spinal, or peripheral nerve block. In some embodiments, the subject is a pediatric subject.

Additional embodiments are described herein.

BRIEF DESCRIPTION OF THE DRAWINGS

FIG. 4A. Schematic of target nerve in the hind limb of the cat. FIG. 4B. In vivo experimentation.

DETAILED DESCRIPTION

Figure 1:
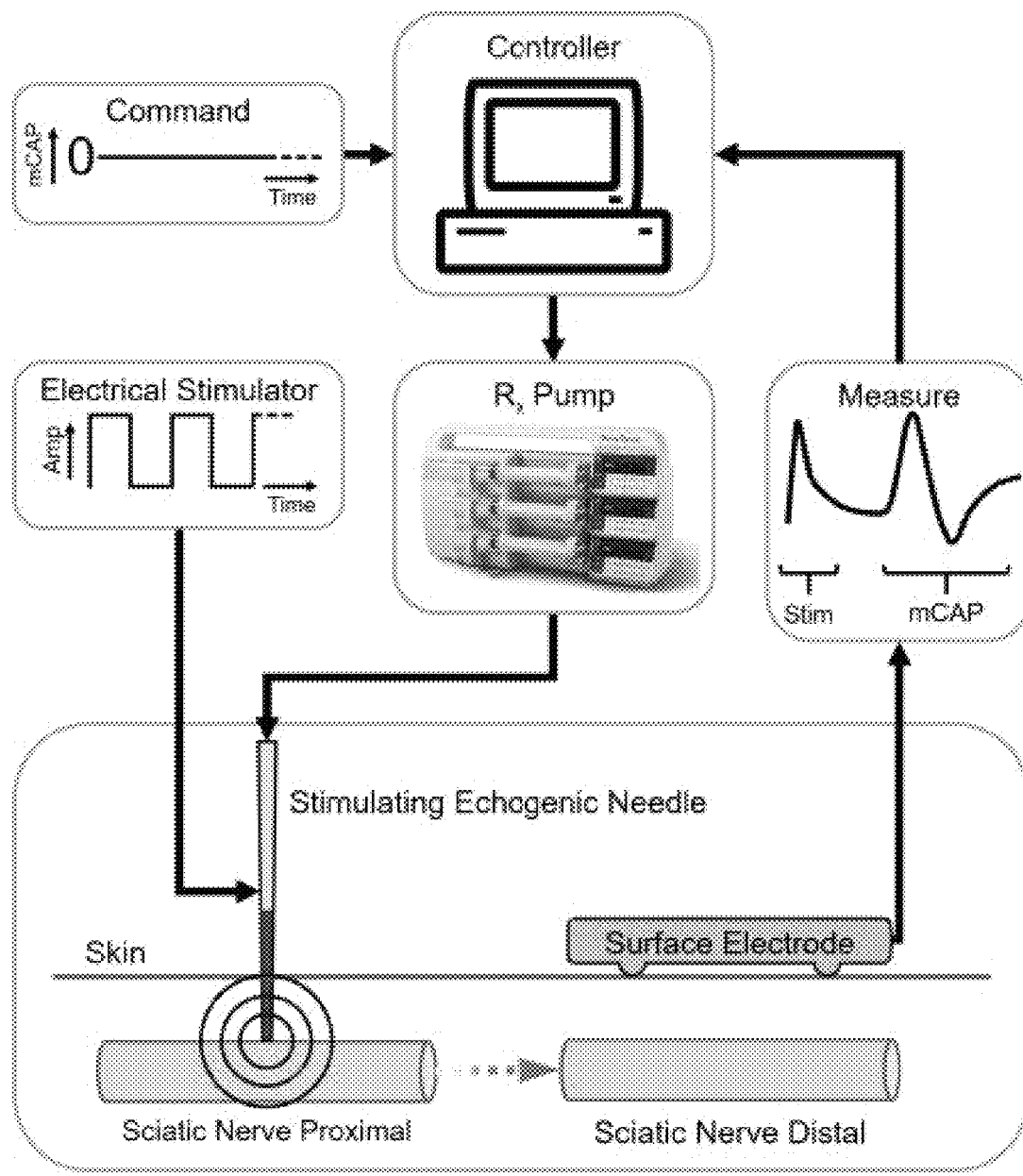
FIG. 1 shows pRA computer controlled anesthetic titration.

Provided herein are devices, systems, and methods for delivery of regional anesthesia. In particular, provide herein are devices designed for computer-controlled delivery and dosage of anesthesia.

When possible, regional anesthesia is generally preferred over general anesthesia. Although this is especially true with respect to pediatric care, pediatric regional anesthesia dosing guidelines are mostly unknown and based only on expert conjecture (Suresh et al., 2015; herein incorporated by reference in its entirety). Further complicating this problem, systemic toxic reactions present very differently in children than adults. In addition, pediatric regional anesthesia is mostly performed under deep sedation, making it yet more difficult to qualify and quantify dosage efficacy. To address these pediatric-specific problems, provided herein is a device that can measure the effectiveness of local anesthetic dosage in children. The solution involves a computer-controlled electromechanical system designed to administer anesthetic solution, in real time, based on monitoring the compound action potential of the target nerve. Although some embodiments herein are described for use with pediatric subjects, and some embodiments have particular advantages with such patients, embodiments herein are not limited to pediatric subjects and may find use with infant, child, adolescent, teenage, adult, and/or elderly subjects.

The majority of the work establishing the relationship between compound action potential shape and anesthetic agents has been performed in-vitro, based on the seminal work of Gasser and Erlanger (Gasser & Erlanger, 1929; herein incorporated by reference in its entirety). In order to translate this work to pediatrics, experiments conducted during development of embodiments herein demonstrate that the shape of the compound action potential is controllable by anesthetic agents in vivo. Experiments were conducted during development of embodiments herein, in which, after exposing the major branch of the sciatic nerve in a cat, a custom drug delivery cuff was implanted which allows for the control of both volume and concentration of the anesthetic agent on the nerve. Electrodes are present at each end of the cuff: one to deliver an electrical stimulus and one to record compound action potential from the nerve. After surgery, a control period of action potentials was measured followed by series of drug exposure and washout following an increase of concentration and volume.

Provided herein is the construction and implementation of the drug delivery cuff and use data therefrom. Experiments conducted during development of embodiments herein indicate that the in vitro methods developed by Gissen and colleagues are replicated in vivo using systems, devices and methods herein. Data shows that the shape of the compound action potential is precisely controlled by delivering a controlled volume and concentration of an anesthetic agent around a peripheral nerve in-vivo and in real-time. Experiments conducted during development of embodiments herein demonstrate that the devices described herein, and the compound action potentials measured thereby, provide a control variable to titrate anesthetic agents for regional anesthesia in-vivo and in real time. In some embodiments, devices and methods herein provide more precise and safer anesthesia dosing, increasing patient safety, and improving outcomes, particularly for pediatric patients.

The devices, systems, and methods described herein provide a computer-controlled electromechanical system designed to administer anesthetic solution (e.g., in real time) based on monitoring the compound action potential (CAP) of the target nerve.

Individualized and controlled anesthetic titration provided by the compositions and methods described herein greatly improves pRA safety. The unique approaches herein merge basic science with FDA approved pediatric tools.

In some embodiments, provided herein are drug delivery and monitoring devices, comprising (1) a nerve stimulation element (e.g., electrode (e.g., mounted on or integrated into a cuff)), (2) a recording element (e.g., electrode (e.g., mounted on or integrated into a cuff)), and (3) a drug delivery element (e.g., mounted on or integrated into a cuff). In some embodiments, provided herein are drug delivery and monitoring devices, comprising: at least two cuffs (e.g., each comprising at least one electrode) configured to stimulate a nerve and record a compound action potential; and a drug delivery cuff configured to deliver a drug directly to a nerve. In some embodiments, the drug delivery cuff comprises one of more of a right buckle, a left buckle, a suture guide, a drug output, a drug input, or a drug reservoir. In some embodiments, the cuffs are stimulation and recording cuffs. In some embodiments, the stimulation cuff comprises a stimulating echogenic needle configured to deliver an electrical current directly to a nerve. In some embodiments, the electrical current is between 1 and 10 amps (e.g., 1, 2, 3, 4, 5, 6, 7, 8, 9, 10, or a fraction thereof). In some embodiments, the recording cuff comprises a surface electrode.

Figure 7:
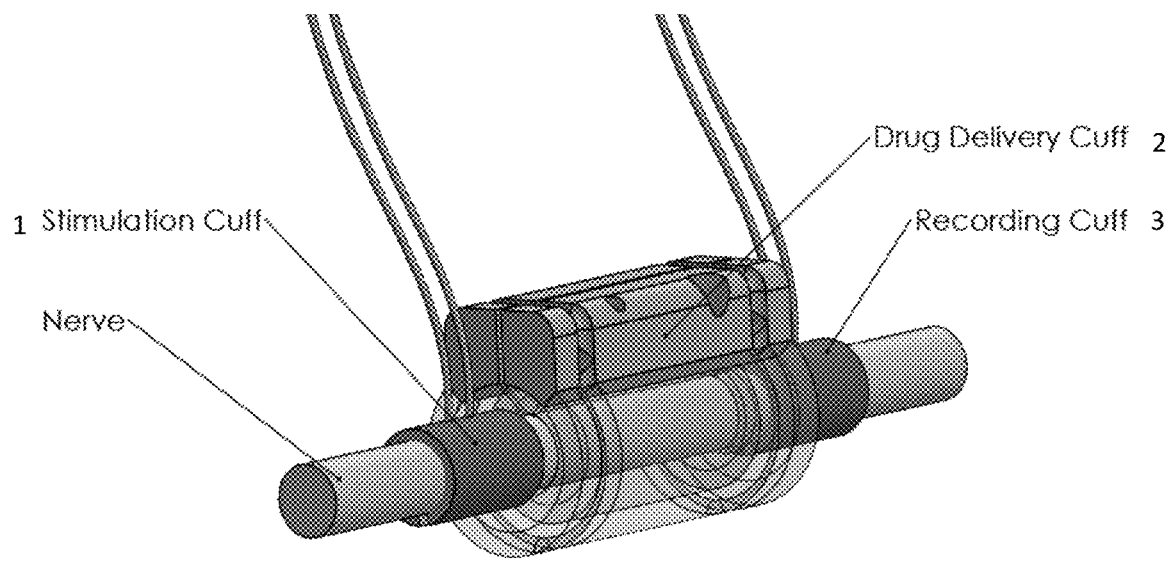
FIG. 7 shows an exemplary device of embodiments of the present disclosure.

Exemplary devices are shown in FIGS. 1-3 and 7-8. FIG. 7 shows an overview of an exemplary device. Shown are stimulation cuff 1, drug delivery cuff 2, and recording cuff 3.

Figure 8:
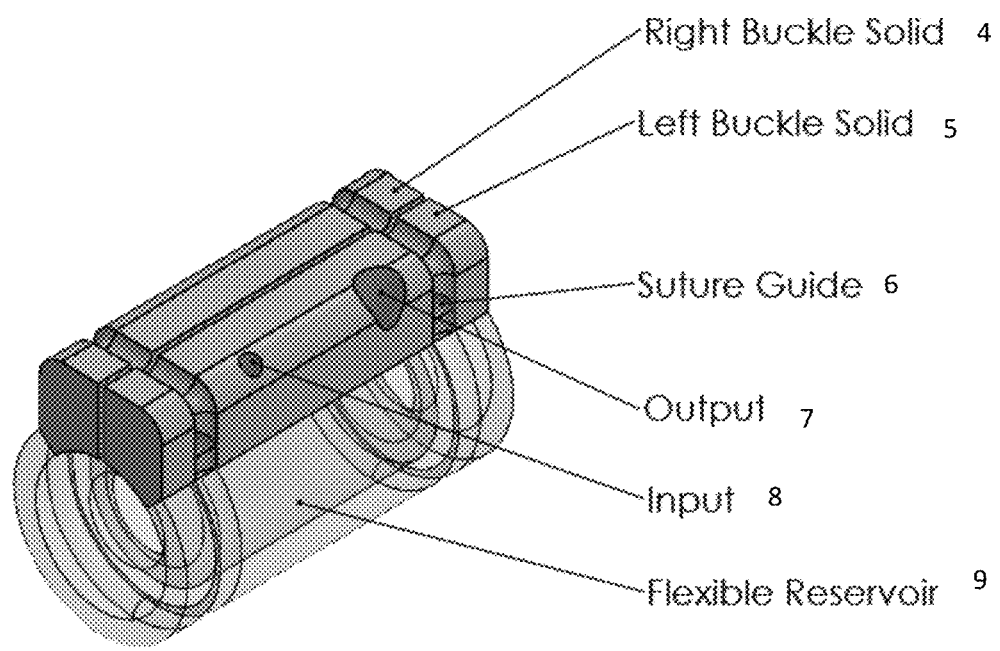
FIG. 8 shows a close up of a drug delivery cuff of an exemplary device of embodiments of the present disclosure.

FIG. 8 shows a close up of drug delivery cuff 2. Shown are right buckle 4, left buckle 5, suture guide 6, output 7, input 8, and drug reservoir 9.

In some embodiments, devices are not limited to those depicted in the figures. Other exemplary devices comprise stimulation, recording, and/or drug delivery elements that are not cuffs. In some embodiments, a device is secured to and/or adjacent to a nerve via any suitable securing element (e.g., cuff, etc.).

Further embodiments provide a system, comprising: the devices described herein; and a computer system configured to calculate compound action potentials and determine a drug dose based on the compound action potentials. In some embodiments, the computer system is further configured to control the drug delivery cuff. In some embodiments, the level of anesthesia is adjusted to keep the compound action potential below a threshold level (e.g., 0.1 V or lower) (e.g., less than 0.1, 0.09, 0.08, 0.07, 0.06, 0.05, 0.04, 0.03, 0.02, 0.009, 0.005, 0.003, or lower), although other values are contemplated. The present disclosure is not limited to particular drugs, although the device is exemplified with anesthesia. Any suitable regional anesthesia may be utilized (e.g., bupivacaine, lidocaine, etc.). Other drugs may be utilized. For example, in some embodiments, a drug (e.g., anesthetic agent) is selected from the group consisting of ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquine, dimethocaine, diperodone, dycyclonine, ecgonidine, ecgonine, ethyl chloride, etidocaine, beta-eucaine, euprocine fenalcomine, formocaine, hexylcaine, hydroxytetracaine, isobutyl p-aminobenzoate, leucinocaine mesylate, levoxadrol, lidocaine, mepryl-caine, metabutoxycaine, methyl chloride, myrtecaine, naepaine, octacaine, orthocaine, oxethazaine, parethoxy-caine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycane, trimecaine, zolamine, or a salt thereof, or mixtures thereof. The device finds use on any nerve. In some embodiments, the device is utilized for epidural, spinal, or peripheral nerve block.

Yet other embodiments provide a method of delivering a regional drug to a subject, comprising: contacting the system described herein with a nerve of a subject; and delivering the drug to the subject using the system. In some embodiments, the drug is regional anesthesia. In some embodiments, the patient is a pediatric patient, although the device finds use in patients of all ages.

EXPERIMENTAL

Example 1

Figure 5:
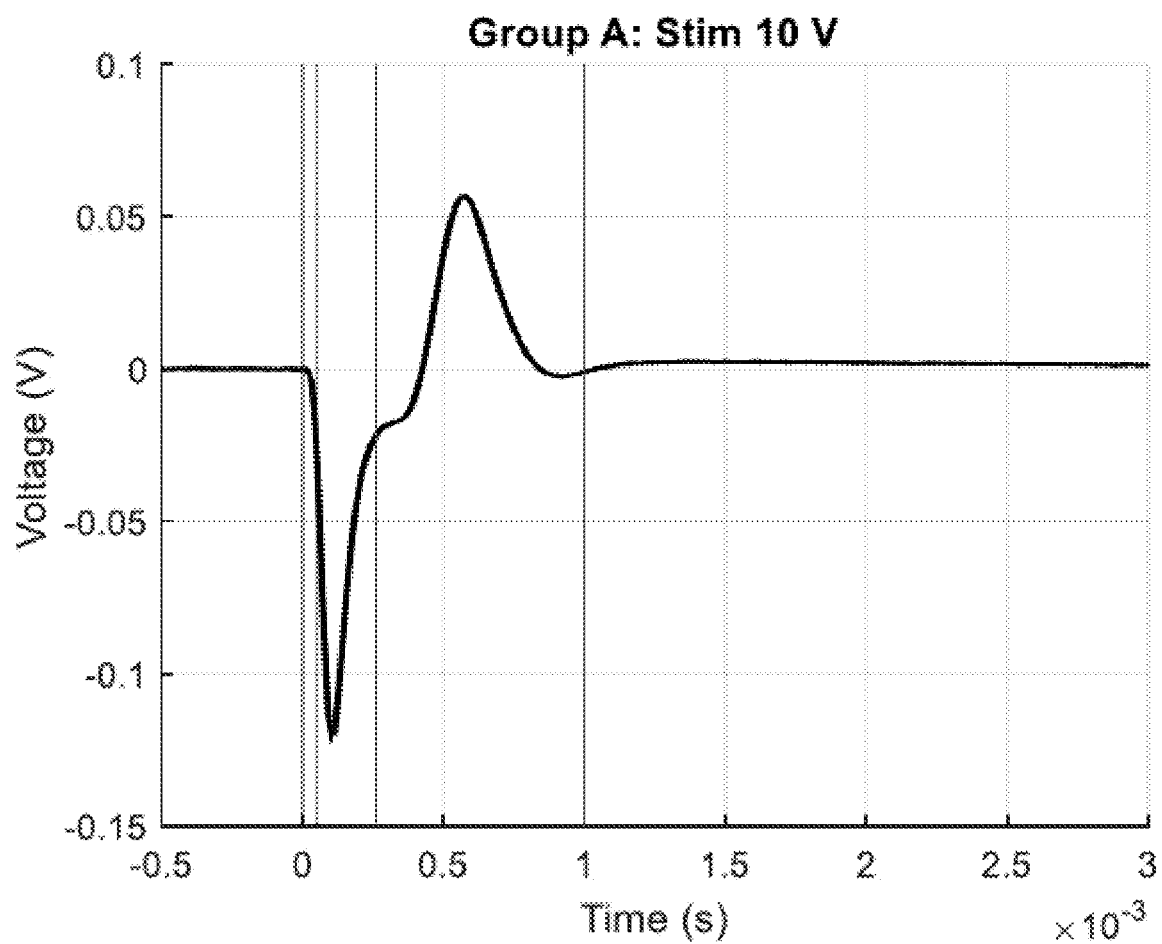
FIG. 5 shows a graph of group A response for 10 V stimulus. Maximum Response is extracted by taking a 1 ms average around the maximum response.
Figure 6:
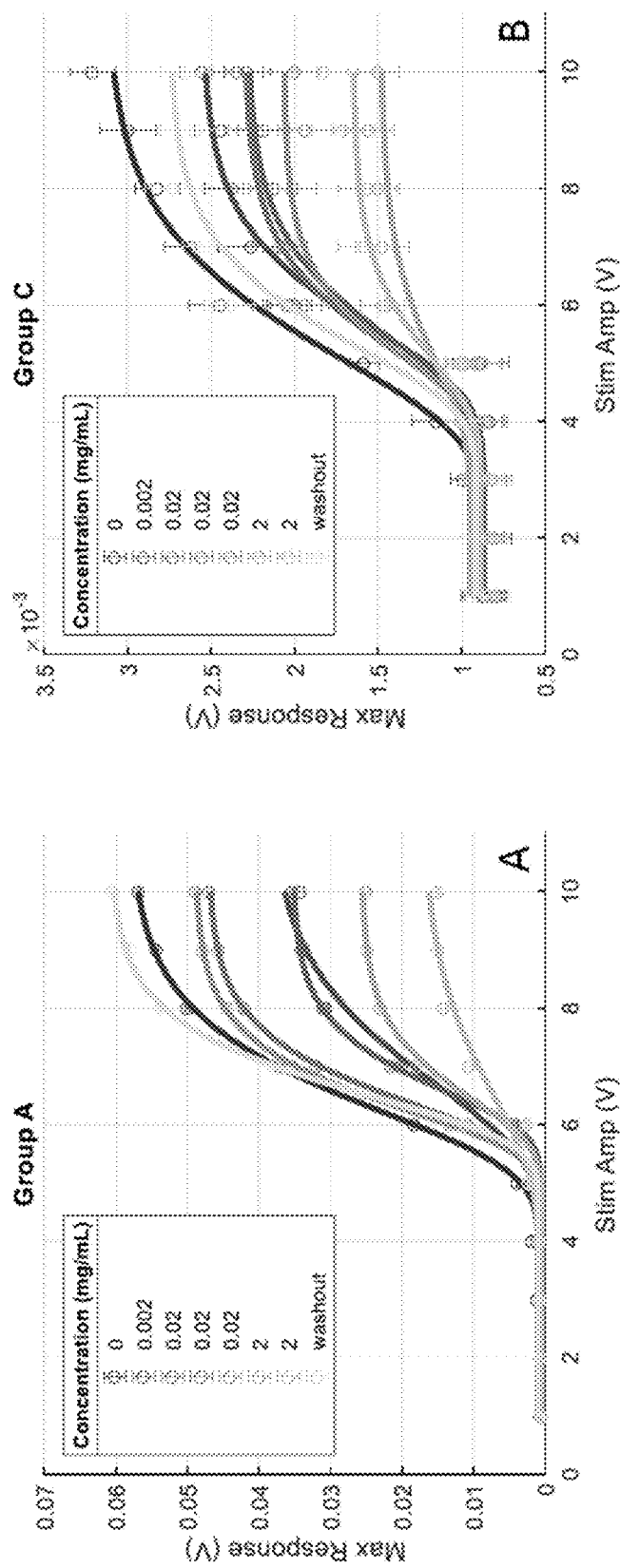
FIG. 6 shows a graph of maximum compound action potential (CAP) response at different stimulation amplitudes for different concentration of anesthetic. A. Shows data for Group A fibers. B. Shows data for group C fibers.

Protocol
  Square Wave Stimulus
    Amplitude Range 1:1:10 V
    Inter Stimulation Interval: 1 s
    Stimulation Width Range: 0.05, 0.1 & 1 ms
  Drug Delivery
    Concentration: 0, 0.002, 0.02 and 0.2 mg/mL
    5 min exposure at each drug concentration
    Washout of drug always returned action potential (AP) amplitudes to at least 90% of control.
  Results (FIGS. 5-6) demonstrate the usefulness and efficacy of the devices and methods herein for therapeutic delivery and monitoring in vivo. Results further demonstrate precise control the shape of the compound action potential by delivering a controlled volume and concentration of an anesthetic agent around a peripheral nerve in-vivo and in real-time (FIG. 6).

Example 2

Figure 2:
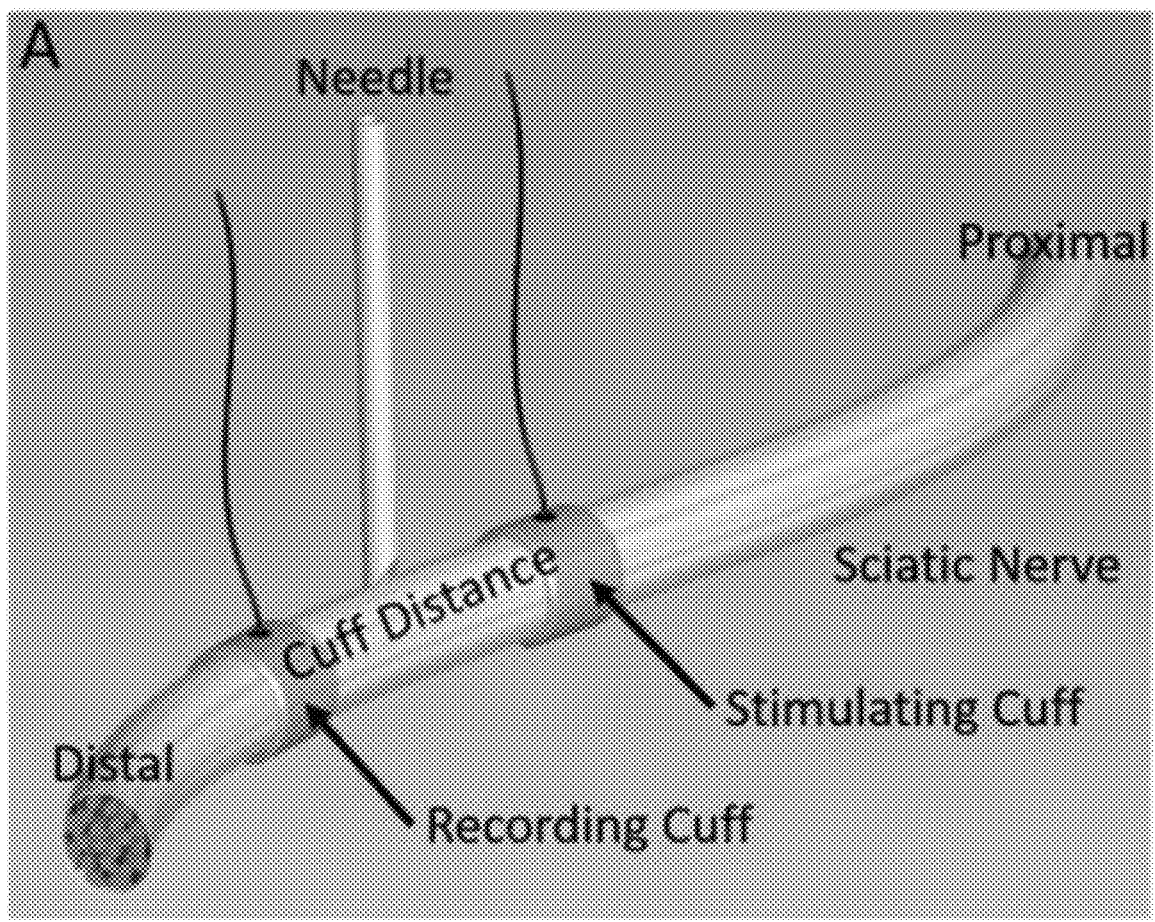
FIG. 2 shows A) Schematic of cuff experiments. B) maximum compound action potential (mCAP) change with respect to anesthetic bolus.
Figure 2:
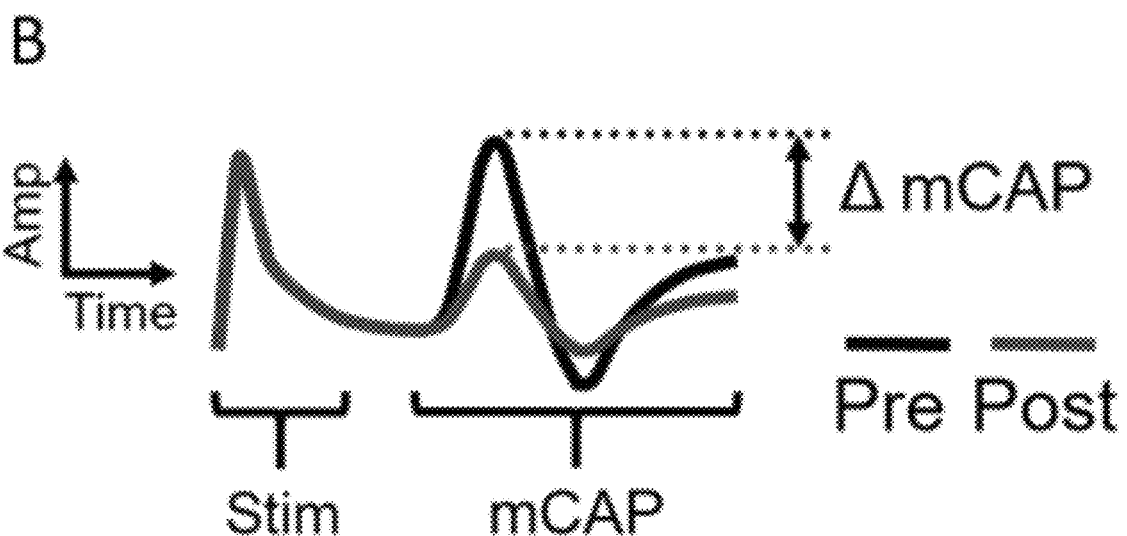
Figure 3:
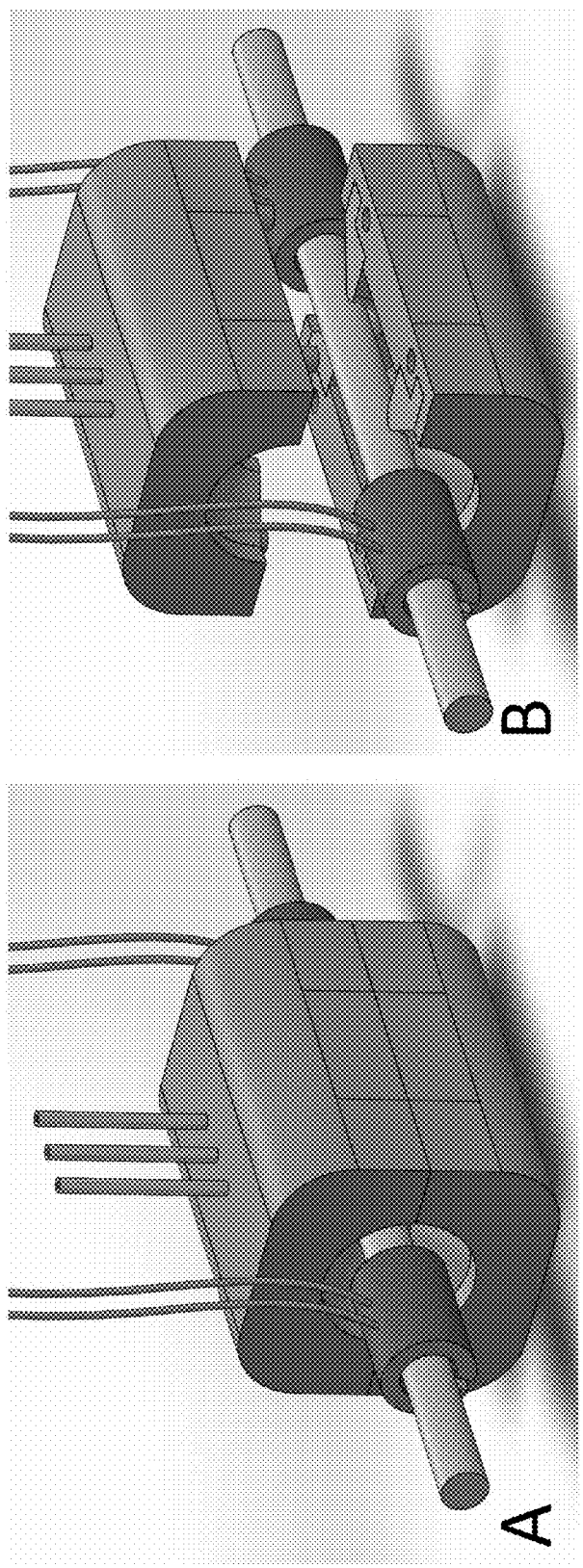
FIG. 3 shows a solid model of drug delivery cuff. A. Fully assembled view. B. Exploded view. On one side of the cuff is a stimulating electrode and one the other side of the cuff is a recording electrode.
Figure 4A:
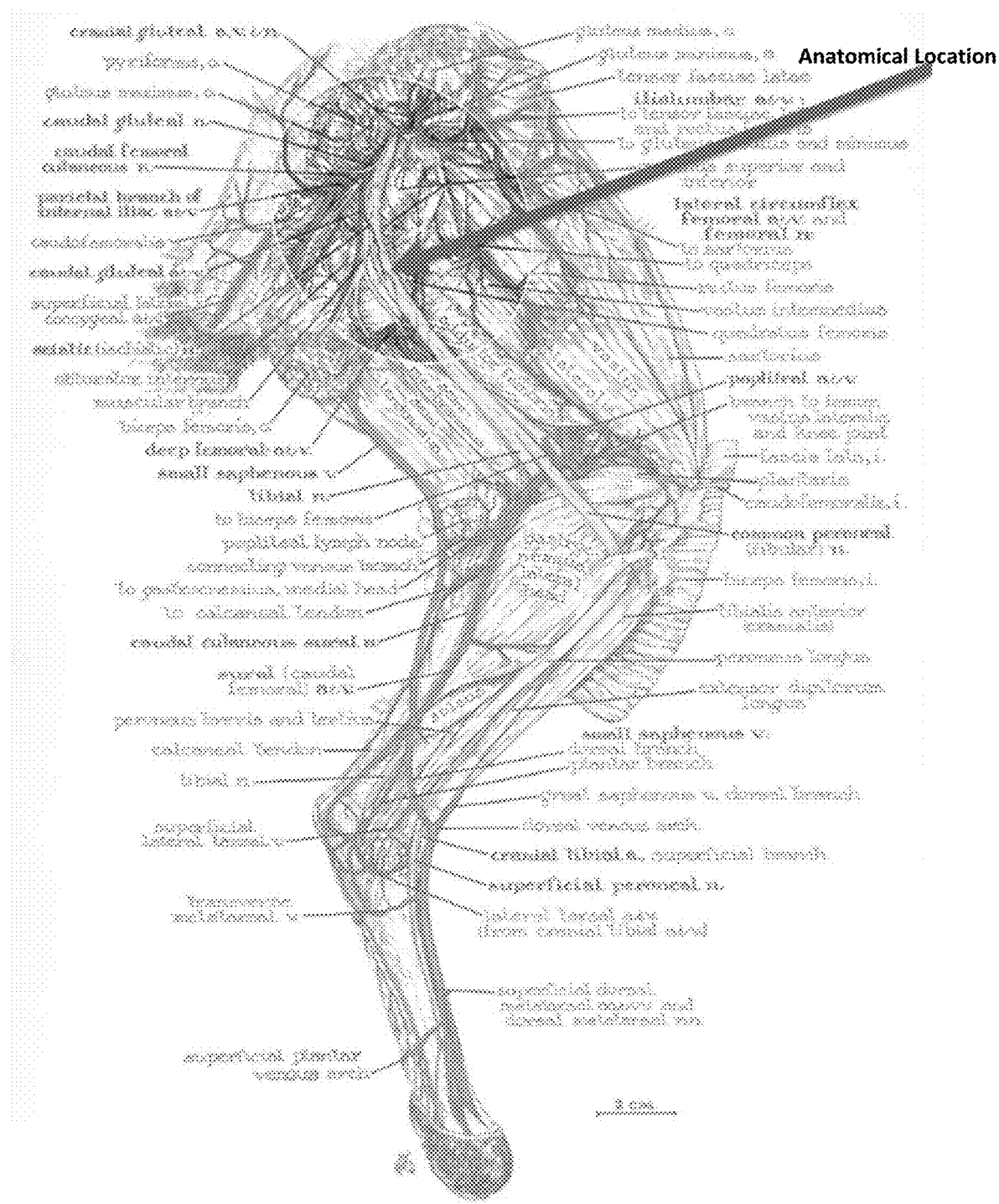
FIGS. 4A-B show an exemplary experimental Setup.
Figure 4B:
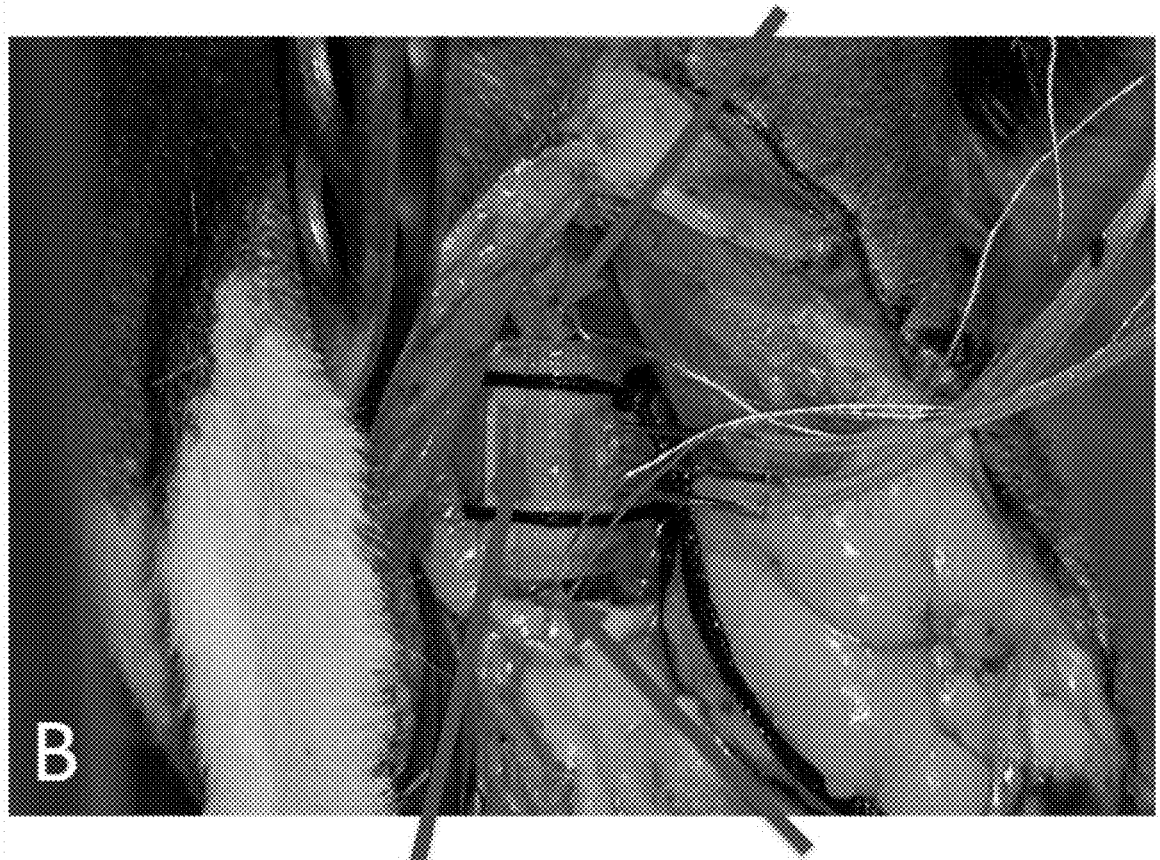

Two nerve cuff electrodes are placed on the sciatic nerve in the cat (cSN) at a known distance from each other (FIG. 2-A). Prior to the anesthetic injection, the mCAP of the cSN is measured and maintained[11]. Equidistant to the cuffs, the needle is placed at the epineurium and ropivacaine is injected. The time of injection is noted as well as the concentration of the drug.

FIG. 1 shows exemplary systems including, for example, a computer controlled electromechanical system designed to administer anesthetic solution, in real time, based on monitoring the maximum compound action potential (mCAP) of the target nerve. FIG. 2 shows that electrically generated mCAPs can predictably be altered by cocaine concentrations[7] (see FIG. 2-B).

Using the above system without anesthetic, mCAPs are measured while the skin of the hind limb is progressively pinched at increasing force.

To validate this pediatric-compatible approach, nerve cuffs will be chronically implanted on the cSN. After full recovery we will guide a stimulating echogenic needle to the cSN equidistant from each cuff using ultrasound, and place a recording surface electrode on the medial aspect of the thigh above the knee. Tests of a simple controlling algorithm based on suppressing mCAPs (see FIG. 1 and FIG. 2-B) are performed using anesthetic time constants measured as above.

Example 3

Nerve Block

Figure 9:
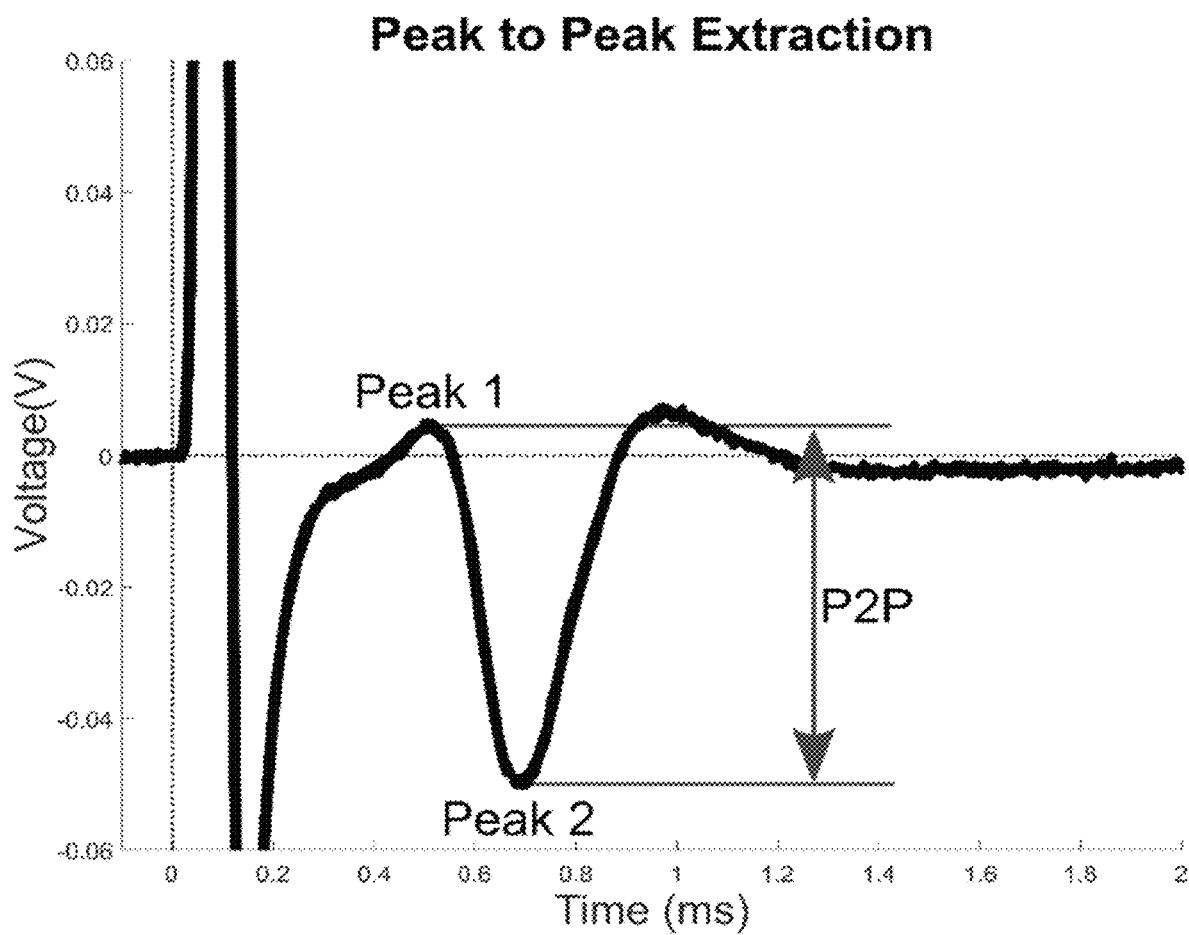
FIG. 9 shows an exemplary recording electrode trace and demonstrates the measurement of peak to peak response from the raw data.

To extract peak-to-peak values from raw electrode data, the compound action potential is identified from the recording electrode trace for each square pulse. The first two peaks of the biphasic response are identified and the difference between the values at these two peaks is determined (FIG. 9; P2P=Peak1−Peak2).

Figure 10:
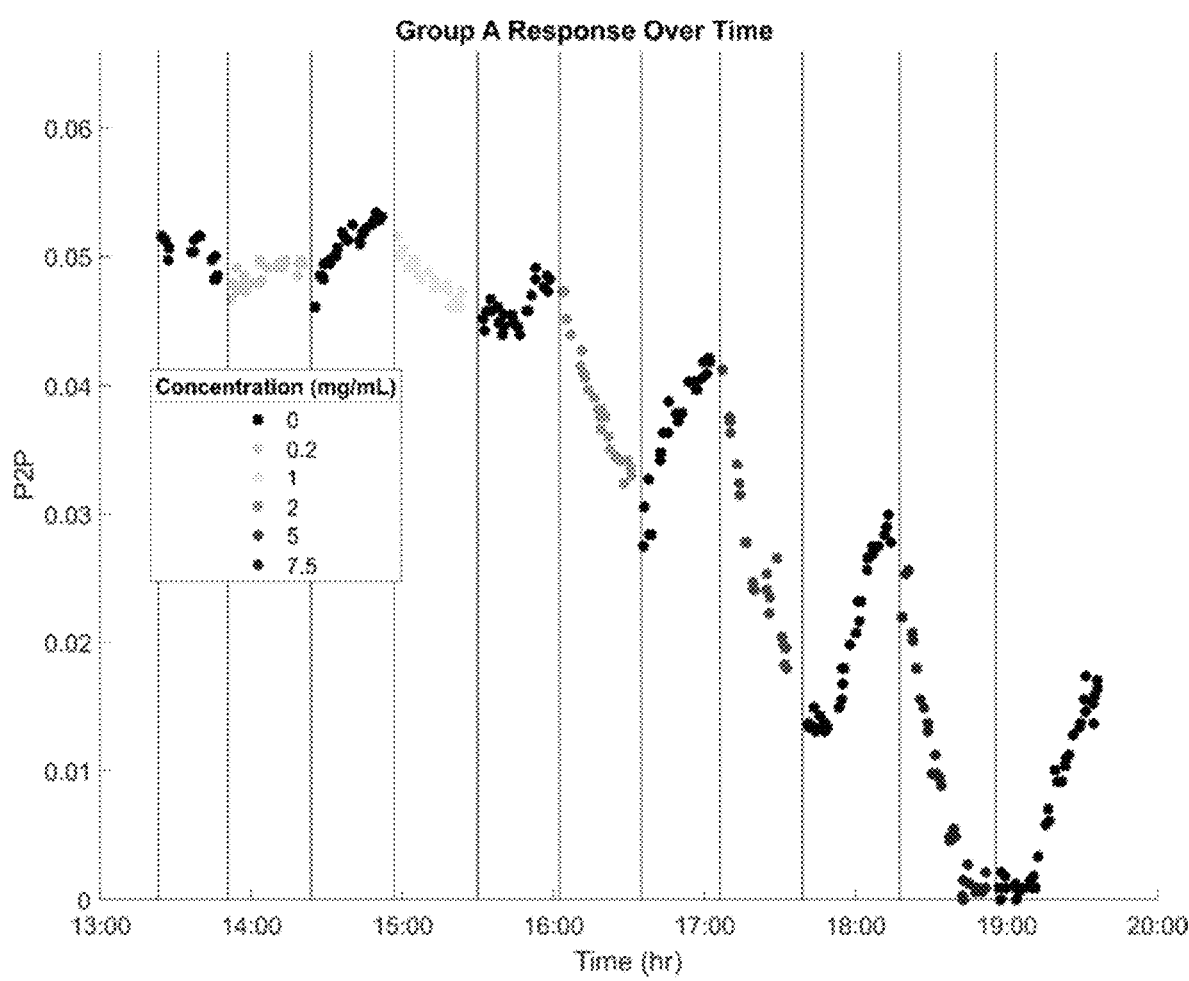
FIG. 10 shows a graph depicting peak to peak response over time for subjects receiving varying concentrations of therapeutic.

To analyze activity over time, a temporal activity curve was deduced by plotting the peak to peak values with respect to experimental time (FIG. 10).

Figure 11:
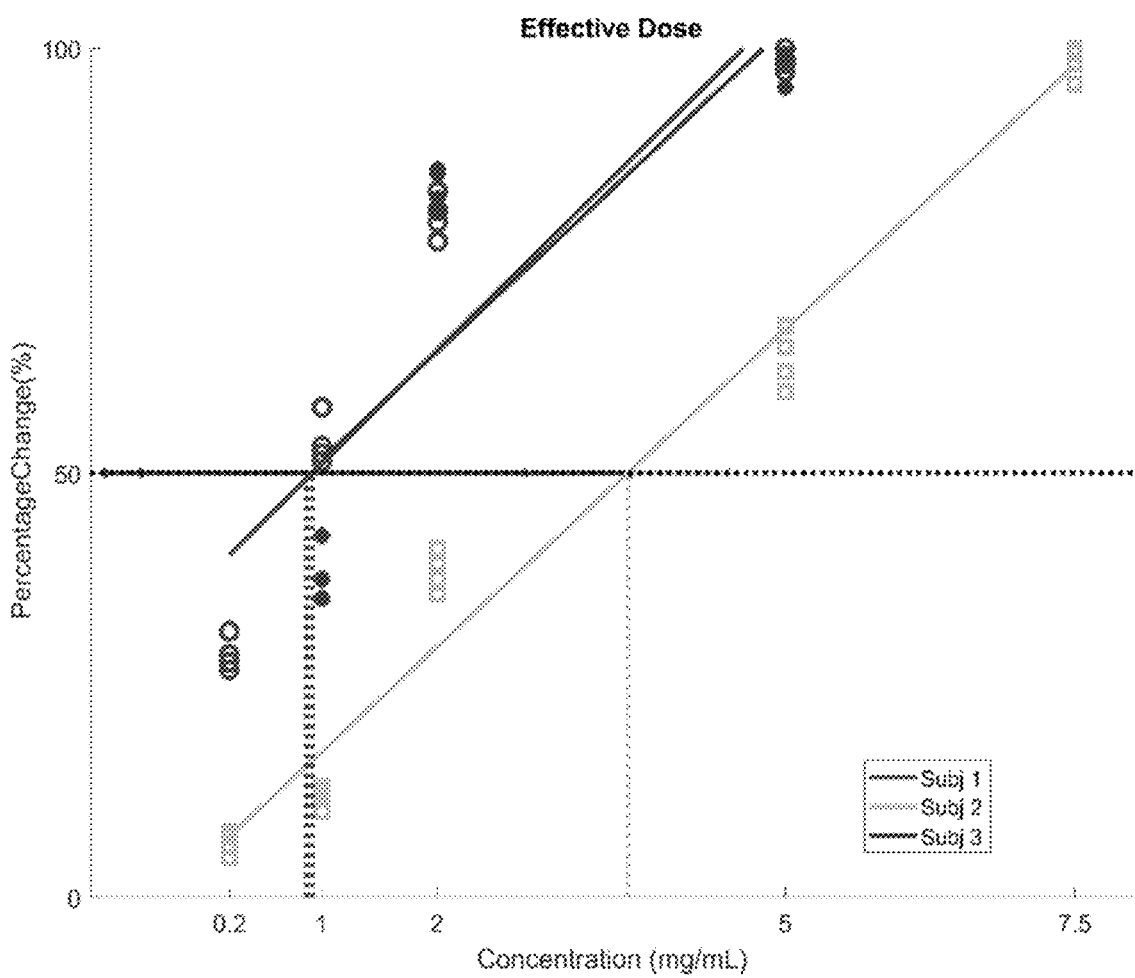
FIG. 11 shows effective dose curves three subjects.

The effective dose curve relates percentage change of the peak to peak values to the concentration of the anesthetic drug. The effective dose at 50% (ED50) is the drug concentration at which the peak to peak values will be reduced by 50%. The effective dose values for the curve are calculated using the following equation:

$$ED = 100 \times \left(\frac{P2P - P2P_0}{P2P_0}\right) \quad \text{Eq. 1}$$

where P2P is the peak to peak value at a given time and $P2P_0$ is the average of the initial peak to peak values prior the introduction of drugs. The effective dose at 50% is deduced by fitting a linear polynomial curve (y=ax+b) to the effective dose values and calculating the concentration at the peak to peak reduction of 50% (FIG. 11).

REFERENCES

The following references, some of which are cited above by number, are herein incorporated by reference in their entireties.
1. Tsui, B. & Suresh, S. *Pediatric Atlas of Ultrasound-and Nerve Stimulation-Guided Regional Anesthesia.* (Springer, 2015).
2. Jöhr, M. Regional anaesthesia in neonates, infants and children. *Eur. J. Anaesthesiol.* 32, 289-297 (2015).

3. Suresh, S., Long, J., Birmingham, P. K. & De Oliveira, G. S. Are caudal blocks for pain control safe in children? an analysis of 18,650 caudal blocks from the Pediatric Regional Anesthesia Network (PRAN) database. *Anesth. Analg.* 120, 151-6 (2015).
4. Suresh, S., Schaldenbrand, K., Wallis, B. & De Oliveira, G. S. Regional anaesthesia to improve pain outcomes in paediatric surgical patients: A qualitative systematic review of randomized controlled trials. *Br. J. Anaesth.* 113, 375-390 (2014).
5. Walker, B. J. et al. Peripheral nerve catheters in children: an analysis of safety and practice patterns from the pediatric regional anesthesia network (PRAN). *Br. J. Anaesth.* 115, 457-62 (2015).
6. Catterall, W. A. & Mackie, K. in *Goodman & Gilman's The Pharmacological Basis of Therapeutics,* 12e (eds. Brunton, L. L., Chabner, B. A. & Knollmann, B. C.) (The McGraw-Hill Companies, 2011).
7. Gasser, H. S. & Erlanger, J. The role of fiber size in the establishment of a nerve block by pressure or cocaine. *Am. J. Physiol.* 88, 581-591 (1929).
8. McClure, J. H. Ropivacaine. *Br. J. Anaesth.* 76, 300-307 (1996).
9. Gissen, A. J., Covino, B. G. & Gregus, J. Differential sensitivities of mammalian nerve fibers to local anesthetic agents. *Anesthesiology* 53, 467-474 (1980).
10. Feldman, H. S. & Covino, B. G. Comparative motor-blocking effects of bupivacaine and ropivacaine, a new amino amide local anesthetic, in the rat and dog. *Anesth. Analg.* 67, 1047-52 (1988).
11. Metso, A. J., Palmu, K. & Partanen, J. V. Compound nerve conduction velocity—A reflection of proprioceptive afferents. *Clin. Neurophysiol.* 119, 29-32 (2008).
12. Preston, D. C. & Shapiro, B. E. in *Electromyography and Neuromuscular Disorders* 19-35 (Saunders, 2012
13. Patel, Y. A., & Butera, R. J. (2015). Differential fiber-specific block of nerve conduction in mammalian peripheral nerves using kilohertz electrical stimulation. Journal of Neurophysiology, 113(10), 3923-9. http://doi.org/10.1152/jn.00529.2014
14. Wildsmith, J. A. W., Brown, D. T., Paul, D., & Johnson, S. (1989). Structure-activity relationships in differential nerve block at high and low frequency stimulation. British Journal of Anaesthesia, 63, 444-452.

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

The invention claimed is:

1. A drug delivery and monitoring device having proximal and distal ends and configured for positioning along a nerve, the device comprising:
    (a) a nerve-stimulating element located at the proximal end of the device and comprising a stimulation cuff and a first electrode, wherein the first electrode is configured to deliver an electric stimulus;
    (b) a recording element located at the distal end of the device and comprising a recording cuff and a second electrode, wherein the second electrode is configured to detect a compound action potential; and
    (c) a drug-delivery element located between the nerve-stimulating element and the recording element.

2. The device of claim 1, wherein the drug-delivery element comprises a drug-delivery cuff for attachment of the device to the nerve.

3. The device of claim 2, wherein said drug-delivery cuff comprises one or more of a right buckle, a left buckle, a suture guide, a drug output, a drug input, or a drug reservoir.

4. The device of claim 1, wherein said stimulation cuff comprises a stimulating echogenic needle.

5. The device of claim 4, wherein said echogenic needle is configured to deliver an electrical current directly to the nerve.

6. The device of claim 1, wherein said electrical current is between 1 and 10 amps.

7. The device of claim 1, wherein said recording cuff comprises a surface electrode.

8. A system, comprising:
    (a) a drug delivery and monitoring device having proximal and distal ends and configured for positioning along a nerve, the device comprising: (i) a nerve-stimulating element located at the proximal end of the device and comprising a first electrode, wherein the first electrode is configured to deliver an electric stimulus; (ii) a recording element located at the distal end of the device and comprising a second electrode, wherein the second electrode is configured to detect a compound action potential; and (iii) a drug-delivery element located between the nerve-stimulating element and the recording element; and
    (b) a computer device configured to record compound action potentials, make calculations based thereon, and control said drug-delivery element.

9. The system of claim 8, wherein the computer device is further configured to determine a drug dose based on said compound action potentials.

10. The system of claim 8, wherein a level of anesthesia is adjusted to keep the compound action potentials below a threshold level.

11. The system of claim 10, wherein said threshold level is 0.1 V.

12. A method of delivering a regional drug to a subject, comprising:
    a) contacting a nerve of the subject with the drug delivery and monitoring device of the system of claim 8;
    b) delivering the drug to the nerve using said system; and
    (c) monitoring compound action potentials; and
    (d) adjusting a level of the drug delivered to the nerve based on said compound action potentials.

13. The method of claim 12, wherein said drug is regional anesthesia.

14. The method of claim 13, wherein said regional anesthesia is epidural, spinal, or peripheral nerve block.

* * * * *